(12) United States Patent
Park et al.

(10) Patent No.: US 10,247,739 B2
(45) Date of Patent: Apr. 2, 2019

(54) METHOD FOR IMMUNOLOGICAL MEASUREMENT USING A HAPTEN AND ANTIBODY BINDING TO THE HAPTEN AS REFERENCE ANTIBODY AND DEVICE FOR IMMUNOLOGICAL MEASUREMENT USING THE REFERENCE ANTIBODY

(71) Applicant: SK TELECOM CO., LTD., Seoul (KR)

(72) Inventors: Sunyoung Park, Seoul (KR); Jeongryul Kim, Gunpo (KR); Seong Woo Kim, Seongnam (KR); Kum-Joo Shin, Seoul (KR); Ji-Chul Lee, Gwangmyeong (KR)

(73) Assignee: SK TELECOM CO., LTD., Seoul (KR)

( * ) Notice: Subject to any disclaimer, the term of this patent is extended or adjusted under 35 U.S.C. 154(b) by 189 days.

(21) Appl. No.: 15/034,323

(22) PCT Filed: Oct. 31, 2014

(86) PCT No.: PCT/KR2014/010356
§ 371 (c)(1),
(2) Date: May 4, 2016

(87) PCT Pub. No.: WO2015/072686
PCT Pub. Date: May 21, 2015

(65) Prior Publication Data
US 2016/0291038 A1    Oct. 6, 2016

(30) Foreign Application Priority Data

Nov. 13, 2013 (KR) .................. 10-2013-0137770

(51) Int. Cl.
*G01N 33/78* (2006.01)
*G01N 33/543* (2006.01)
*G01N 33/68* (2006.01)

(52) U.S. Cl.
CPC .......... *G01N 33/78* (2013.01); *G01N 33/543* (2013.01); *G01N 33/6854* (2013.01)

(58) Field of Classification Search
CPC ... G01N 33/543; G01N 33/6854; G01N 33/78
See application file for complete search history.

(56) References Cited

U.S. PATENT DOCUMENTS

| | | | | |
|---|---|---|---|---|
| 5,362,655 A | * | 11/1994 | Schenk | ............ G01N 33/54306 435/2 |
| 5,573,922 A | | 11/1996 | Hoess | |
| 2003/0022246 A1 | | 1/2003 | Ogura | |
| 2005/0239151 A1 | | 10/2005 | Ipsen | |
| 2007/0172963 A1 | * | 7/2007 | Krauth | ................. G01N 33/558 436/514 |
| 2008/0289068 A1 | * | 11/2008 | Danks | ................. G01N 33/558 800/298 |
| 2012/0070908 A1 | | 3/2012 | Suri | |
| 2012/0263796 A1 | * | 10/2012 | Plavina | ............... G01N 33/566 424/530 |
| 2012/0295287 A1 | | 11/2012 | Kellermann | |

FOREIGN PATENT DOCUMENTS

| | | |
|---|---|---|
| EP | 0365818 | 2/1995 |
| EP | 0517325 | 10/2001 |
| JP | 09-061426 | 3/1997 |
| KR | 10-2003-0038057 | 5/2003 |
| KR | 10-0644205 | 11/2006 |
| KR | 10-2007-0094159 | 9/2007 |
| KR | 10-2007-0109099 | 11/2007 |
| KR | 10-2008-0102899 | 11/2008 |
| KR | 10-2011-0003226 | 1/2011 |
| KR | 10-2013-0095530 | 8/2013 |
| WO | 2013/125855 | 8/2013 |

OTHER PUBLICATIONS

Ohashi et al., "One-Step Micro-Elisa for Highly Sensitive Determination of TSH," 14th International Conference on Miniaturized Systems for Chemistry and Life Sciences, Oct. 3-7, 2010, Groningen, The Netherlands.*
State Intellectual Property Office of the P.R.C, Search Report of Application No. 201480065579.8, dated Feb. 14, 2017.

* cited by examiner

*Primary Examiner* — Galina Yakovleva
(74) *Attorney, Agent, or Firm* — Lex IP Meister, PLLC

(57) ABSTRACT

The present invention relates to a method for the immunological measurement using a hapten and an antibody binding to the hapten as a reference antibody, and a device for the immunological measurement using the reference antibody. According to the present invention, the method and the device for the immunological measurement can be used in an immunoassay by reflecting surrounding environments, for example, by reflecting a numerical value in a test zone, which is changed by external factors such as temperatures of a sample and a device, an amount and components of an injected sample, variations of the device, and the like, in a reference zone and changing the numerical value in the test zone, and can be useful in minimizing analysis errors due to a low probability of causing a non-specific reaction with a material in the sample.

16 Claims, 8 Drawing Sheets

Specification includes a Sequence Listing.

```
SEQUENCE LISTING

<160> NUMBER OF SEQ ID NOS: 28

<210> SEQ ID NO 1
<211> LENGTH: 120
<212> TYPE: PRT
<213> ORGANISM: Artificial Sequence
<220> FEATURE:
<223> OTHER INFORMATION: Heavy chain variable region (VH) amino acid
      sequence of reference antibody

<400> SEQUENCE: 1

Ala Val Thr Leu Asp Glu Ser Gly Gly Gly Leu Gln Thr Pro Gly Gly
  1               5                  10                  15

Ala Leu Ser Leu Ile Cys Lys Ala Ser Gly Phe Ser Ile Gly Asp Tyr
             20                  25                  30

Gly Met Gly Trp Met Arg Gln Ala Pro Gly Lys Gly Leu Glu Trp Val
         35                  40                  45

Ala Ser Ile Arg Ser Asp Gly Ser Ser Thr Tyr Tyr Gly Ser Ala Val
     50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Ala Thr Tyr Tyr Cys
                 85                  90                  95

Ala Lys Asp Gly Val Gly Trp Ser Ala Thr Ile Asp Ala Trp Gly His
            100                 105                 110

Gly Thr Glu Val Ile Val Ser Ser
        115                 120

<210> SEQ ID NO 2
<211> LENGTH: 103
<212> TYPE: PRT
<213> ORGANISM: Artificial Sequence
```

```
<220> FEATURE:
<223> OTHER INFORMATION: Light chain variable region (VL) amino acid
      sequence of reference antibody

<400> SEQUENCE: 2

Ala Leu Thr Gln Pro Ser Ser Val Ser Ala Asn Pro Gly Gly Thr Val
1               5                   10                  15

Lys Leu Thr Cys Ser Gly Gly Gly Ser Tyr Gly Trp Tyr Gln Gln
            20                  25                  30

Lys Ser Pro Gly Ser Ala Pro Val Thr Leu Ile Tyr Asn Asn Lys
        35                  40                  45

Arg Pro Ser Asn Ile Pro Ser Arg Phe Ser Gly Ser Lys Phe Gly Ser
    50                  55                  60

Thr Ala Thr Leu Thr Ile Thr Gly Val Gln Ala Glu Asp Glu Ala Val
65                  70                  75                  80

Tyr Phe Cys Gly Ser Thr Asp Ile Arg Ser Thr Pro Ile Phe Gly Ala
                85                  90                  95

Gly Thr Thr Leu Thr Val Leu
            100

<210> SEQ ID NO 3
<211> LENGTH: 10
<212> TYPE: PRT
<213> ORGANISM: Artificial Sequence
<220> FEATURE:
<223> OTHER INFORMATION: CDR1 amino acid sequence of heavy chain
      variable region (HCDR1) of reference antibody

<400> SEQUENCE: 3

Gly Phe Ser Ile Gly Asp Tyr Gly Met Gly
1               5                   10

<210> SEQ ID NO 4
<211> LENGTH: 17
<212> TYPE: PRT
<213> ORGANISM: Artificial Sequence
<220> FEATURE:
<223> OTHER INFORMATION: CDR2 of heavy chain variable region (HCDR2) of
      reference antibody

<400> SEQUENCE: 4

Ser Ile Arg Ser Asp Gly Ser Ser Thr Tyr Tyr Gly Ser Ala Val Lys
1               5                   10                  15

Gly

<210> SEQ ID NO 5
<211> LENGTH: 11
<212> TYPE: PRT
<213> ORGANISM: Artificial Sequence
<220> FEATURE:
<223> OTHER INFORMATION: CDR3 of heavy chain variable region (HCDR3) of
      reference antibody

<400> SEQUENCE: 5

Asp Gly Val Gly Trp Ser Ala Thr Ile Asp Ala
1               5                   10

<210> SEQ ID NO 6
<211> LENGTH: 8
<212> TYPE: PRT
<213> ORGANISM: Artificial Sequence
<220> FEATURE:
<223> OTHER INFORMATION: CDR1 of light chain variable region (LCDR1) of
      reference antibody
```

-continued

```
<400> SEQUENCE: 6

Ser Gly Gly Gly Gly Ser Tyr Gly
1               5

<210> SEQ ID NO 7
<211> LENGTH: 7
<212> TYPE: PRT
<213> ORGANISM: Artificial Sequence
<220> FEATURE:
<223> OTHER INFORMATION: CDR2 of light chain variable region (LCDR2) of
      reference antibody

<400> SEQUENCE: 7

Tyr Asn Asn Lys Arg Pro Ser
1               5

<210> SEQ ID NO 8
<211> LENGTH: 10
<212> TYPE: PRT
<213> ORGANISM: Artificial Sequence
<220> FEATURE:
<223> OTHER INFORMATION: CDR3 of light chain variable region (LCDR3) of
      reference antibody

<400> SEQUENCE: 8

Gly Ser Thr Asp Ile Arg Ser Thr Pro Ile
1               5                   10

<210> SEQ ID NO 9
<211> LENGTH: 72
<212> TYPE: DNA
<213> ORGANISM: Artificial Sequence
<220> FEATURE:
<223> OTHER INFORMATION: PCR forward primer of VH domain

<400> SEQUENCE: 9
ggtcagtcct ctagatcttc cggcggtggt ggcagctccg gtggtggcgg ttccgccgtg      60
acgttggacg ag                                                         72

<210> SEQ ID NO 10
<211> LENGTH: 44
<212> TYPE: DNA
<213> ORGANISM: Artificial Sequence
<220> FEATURE:
<223> OTHER INFORMATION: PCR reverse primer of VH domain

<400> SEQUENCE: 10
ctggccggcc tggccactag tggaggagac gatgacttcg gtcc                      44

<210> SEQ ID NO 11
<211> LENGTH: 38
<212> TYPE: DNA
<213> ORGANISM: Artificial Sequence
<220> FEATURE:
<223> OTHER INFORMATION: PCR forward primer of VL domain

<400> SEQUENCE: 11
gtggcccagg cggccctgac tcagccgtcc tcggtgtc                             38

<210> SEQ ID NO 12
<211> LENGTH: 34
<212> TYPE: DNA
<213> ORGANISM: Artificial Sequence
<220> FEATURE:
<223> OTHER INFORMATION: PCR reverse primer of VL domain
```

<400> SEQUENCE: 12
ggaagatcta gaggactgac ctaggacggt cagg                                   34

<210> SEQ ID NO 13
<211> LENGTH: 42
<212> TYPE: DNA
<213> ORGANISM: Artificial Sequence
<220> FEATURE:
<223> OTHER INFORMATION: PCR forward primer of scFv domain

<400> SEQUENCE: 13
gaggaggagg aggaggaggt ggcccaggcg gccctgactc ag                          42

<210> SEQ ID NO 14
<211> LENGTH: 47
<212> TYPE: DNA
<213> ORGANISM: Artificial Sequence
<220> FEATURE:
<223> OTHER INFORMATION: PCR reverse primer of scFv domain

<400> SEQUENCE: 14
gaggaggagg aggaggagga gctggccggc ctggccacta gtggagg                     47

<210> SEQ ID NO 15
<211> LENGTH: 20
<212> TYPE: DNA
<213> ORGANISM: Artificial Sequence
<220> FEATURE:
<223> OTHER INFORMATION: scFV sequencing forward primer

<400> SEQUENCE: 15
acactttatg cttccggctc                                                   20

<210> SEQ ID NO 16
<211> LENGTH: 20
<212> TYPE: DNA
<213> ORGANISM: Artificial Sequence
<220> FEATURE:
<223> OTHER INFORMATION: scFV sequencing reverse primer

<400> SEQUENCE: 16
caaaatcacc ggaaccagag                                                   20

<210> SEQ ID NO 17
<211> LENGTH: 85
<212> TYPE: DNA
<213> ORGANISM: Artificial Sequence
<220> FEATURE:
<223> OTHER INFORMATION: PCR forward primer of VH domain for reference
      antibody

<400> SEQUENCE: 17
gctagccgcc accatgggct ggtcctgcat catcctgttc ctggtggcca ccgccaccgg       60
cgccgtgacg ttggacgagt ccggg                                             85

<210> SEQ ID NO 18
<211> LENGTH: 39
<212> TYPE: DNA
<213> ORGANISM: Artificial Sequence
<220> FEATURE:
<223> OTHER INFORMATION: PCR reverse primer of VH domain for reference
      antibody

<400> SEQUENCE: 18
agatggtgcg gtagttttag cggaggagac gatgacttc                39

```
<210> SEQ ID NO 19
<211> LENGTH: 21
<212> TYPE: DNA
<213> ORGANISM: Artificial Sequence
<220> FEATURE:
<223> OTHER INFORMATION: PCR forward primer of heavy chain constant
      region (CH) for reference antibody

<400> SEQUENCE: 19
```
gctaaaacta ccgcaccatc t                                    21

```
<210> SEQ ID NO 20
<211> LENGTH: 21
<212> TYPE: DNA
<213> ORGANISM: Artificial Sequence
<220> FEATURE:
<223> OTHER INFORMATION: PCR reverse primer of CH domain for reference
      antibody

<400> SEQUENCE: 20
```
ggatcccttg ccggccgtcg c                                    21

```
<210> SEQ ID NO 21
<211> LENGTH: 21
<212> TYPE: DNA
<213> ORGANISM: Artificial Sequence
<220> FEATURE:
<223> OTHER INFORMATION: PCR forward primer of heavy chain (HC) for
      reference antibody

<400> SEQUENCE: 21
```
ctagctagcc gccaccatgg g                                    21

```
<210> SEQ ID NO 22
<211> LENGTH: 20
<212> TYPE: DNA
<213> ORGANISM: Artificial Sequence
<220> FEATURE:
<223> OTHER INFORMATION: PCR reverse primer of heavy chain (HC) for
      reference antibody

<400> SEQUENCE: 22
```
gacacctact cagacaatgc                                      20

```
<210> SEQ ID NO 23
<211> LENGTH: 87
<212> TYPE: DNA
<213> ORGANISM: Artificial Sequence
<220> FEATURE:
<223> OTHER INFORMATION: PCR forward primer of VL domain for reference
      antibody

<400> SEQUENCE: 23
```
aagcttgccg ccaccatggg ctggtcctgc atcatcctgt tcctggtggc caccgccacc   60
ggcgccctga ctcagccgtc ctcggtg                              87

```
<210> SEQ ID NO 24
<211> LENGTH: 39
<212> TYPE: DNA
<213> ORGANISM: Artificial Sequence
<220> FEATURE:
<223> OTHER INFORMATION: PCR reverse primer of VL domain for reference
      antibody

<400> SEQUENCE: 24
```

```
cacggttggg gctgcatcgg ctaggacggt cagggttgt                              39

<210> SEQ ID NO 25
<211> LENGTH: 21
<212> TYPE: DNA
<213> ORGANISM: Artificial Sequence
<220> FEATURE:
<223> OTHER INFORMATION: PCR forward primer of kappa chain constant
      region (Ck) domain for reference antibody

<400> SEQUENCE: 25
gccgatgcag ccccaaccgt g                                                 21

<210> SEQ ID NO 26
<211> LENGTH: 24
<212> TYPE: DNA
<213> ORGANISM: Artificial Sequence
<220> FEATURE:
<223> OTHER INFORMATION: PCR reverse primer of Ck domain for reference
      antibody

<400> SEQUENCE: 26
tctagactaa cactcatttc tgtt                                              24

<210> SEQ ID NO 27
<211> LENGTH: 21
<212> TYPE: DNA
<213> ORGANISM: Artificial Sequence
<220> FEATURE:
<223> OTHER INFORMATION: PCR forward primer of light chain (LC) for
      reference antibody

<400> SEQUENCE: 27
cccaagcttg ccgccaccat g                                                 21

<210> SEQ ID NO 28
<211> LENGTH: 22
<212> TYPE: DNA
<213> ORGANISM: Artificial Sequence
<220> FEATURE:
<223> OTHER INFORMATION: PCR reverse primer of light chain (LC) for
      reference antibody

<400> SEQUENCE: 28
ggacacctag tcagacaaaa tg                                                22
```

METHOD FOR IMMUNOLOGICAL MEASUREMENT USING A HAPTEN AND ANTIBODY BINDING TO THE HAPTEN AS REFERENCE ANTIBODY AND DEVICE FOR IMMUNOLOGICAL MEASUREMENT USING THE REFERENCE ANTIBODY

FIELD OF THE INVENTION

The present invention relates to a method for the immunological measurement using a hapten and an antibody binding to the hapten as a reference antibody, and a device for immunological measurement using the reference antibody.

BACKGROUND OF THE INVENTION

Conventional methods for the immunological measurement using rabbit IgG and anti-rabbit IgG as reference antibodies use biochips in which a probe specifically binding to a material to be tested and a probe specifically binding to a rabbit antibody are fixed in a conjugate zone, a capture antibody against the material to be tested is fixed in a test zone, and an anti-rabbit antibody is fixed in a reference zone (WO 2013/125855). However, when a sample is quantified using the reference antibody, measured values may be varied by factors such as differences in viscosity and components caused by large amounts of materials present in the sample, and non-specific reactions by anti-rabbit antibodies and the like although the same amount of the sample is injected. Also, when conventional reference antibodies are used, errors in amount of the sample upon injection of the sample may occur, and the temperature of the sample and/or device may increase or decrease by an environment in which the sample is measured. Therefore, there is a probability in which the values in the test zone may vary always. In addition, the binding affinity of the antibodies in the test and reference zones may be varied by the factors as described above.

Meanwhile, a hapten is a material against which there are no antibodies in the human body since the material causes no immune response per se. When haptens of toxic components which cannot be present in the human body are used, a non-specific reaction is expected to hardly occur in the sample. Also, antibodies having different affinity constants against the hapten have different antigen binding affinities at various temperatures. However, there is no case in which the antibodies binding to the hapten exhibiting such characteristics are used as reference antibodies as far.

Therefore, the present inventors have developed an method for the immunological measurement including a reference antibody which includes a hapten and an antibody binding to the hapten, wherein the method for the immunological measurement is able to improve accuracy in quantitative measurement by supplementing a result value according to parameters of user environments and reducing a non-specific reaction with a sample. Therefore, the present invention has been completed based on the facts.

SUMMARY OF THE INVENTION

Therefore, it is an aspect of the present invention to provide a method for the immunological measurement capable of improving accuracy in quantitative amount of a sample.

It is another aspect of the present invention to provide a device for the immunological measurement using a reference antibody.

According to one aspect of the present invention, the present invention provides a method for the immunological measurement using a hapten and an antibody binding to the hapten as a reference antibody. Here, the antibody includes i) a heavy-chain variable region CDR1 having an amino acid sequence set forth in SEQ ID NO: 3, ii) a heavy-chain variable region CDR2 having an amino acid sequence set forth in SEQ ID NO: 4, iii) a heavy-chain variable region CDR3 having an amino acid sequence set forth in SEQ ID NO: 5; iv) a light-chain variable region CDR1 having an amino acid sequence set forth in SEQ ID NO: 6, v) a light-chain variable region CDR2 having an amino acid sequence set forth in SEQ ID NO: 7, and vi) a light-chain variable region CDR3 having an amino acid sequence set forth in SEQ ID NO: 8.

According to another aspect of the present invention, the present invention provides a device for the immunological measurement using a reference antibody, which includes a hapten and an antibody binding to the hapten. Here, the antibody includes i) a heavy-chain variable region CDR1 having an amino acid sequence set forth in SEQ ID NO: 3, ii) a heavy-chain variable region CDR2 having an amino acid sequence set forth in SEQ ID NO: 4, iii) a heavy-chain variable region CDR3 having an amino acid sequence set forth in SEQ ID NO: 5; iv) a light-chain variable region CDR1 having an amino acid sequence set forth in SEQ ID NO: 6, v) a light-chain variable region CDR2 having an amino acid sequence set forth in SEQ ID NO: 7, and vi) a light-chain variable region CDR3 having an amino acid sequence set forth in SEQ ID NO: 8.

BRIEF DESCRIPTION OF DRAWINGS

These and/or other objects and features of the invention will become apparent and more readily appreciated from the following description of the embodiments, taken in conjunction with the accompanying drawings of which.

DETAILED DESCRIPTION OF THE INVENTION

Figure 1:
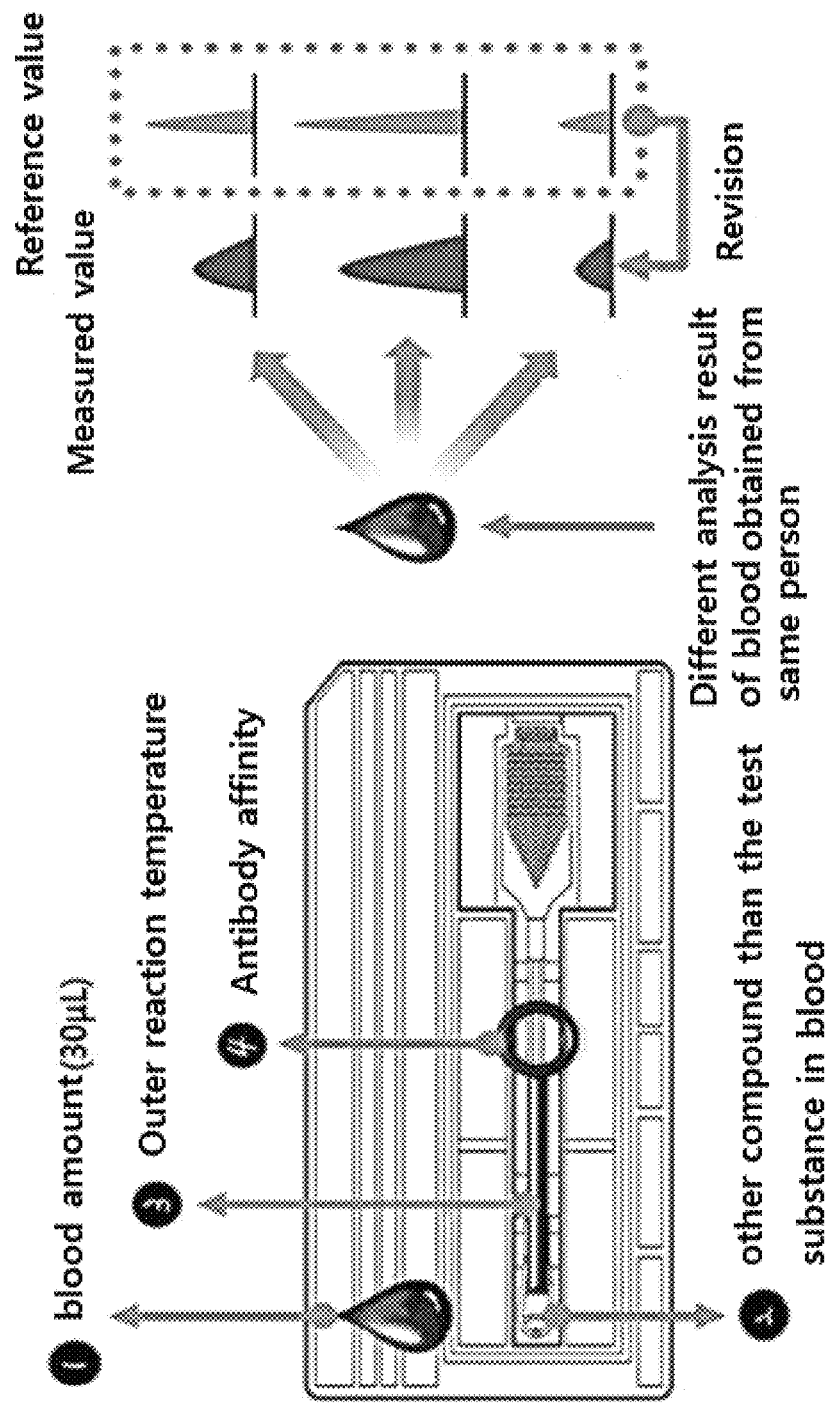
FIG. 1 is a diagram showing factors by which analysis errors are caused in a microfluidics-based quantitative analysis device, showing that different examination results are observed in blood from the same human by the factors.

Hereinafter, the present invention will be described in further detail.

The present invention provides a method for the immunological measurement using a hapten and an antibody binding to the hapten (hereinafter referred to as a hapten antibody) as a reference antibody. Specifically, the present invention provides a method for the immunological measurement using a hapten and an antibody binding to the hapten as a reference antibody, wherein the antibody includes i) a heavy-chain variable region CDR1 having an amino acid sequence set forth in SEQ ID NO: 3, ii) a heavy-chain variable region CDR2 having an amino acid sequence set forth in SEQ ID NO: 4, iii) a heavy-chain variable region CDR3 having an amino acid sequence set forth in SEQ ID NO: 5; iv) a light-chain variable region CDR1 having an amino acid sequence set forth in SEQ ID NO: 6, v) a light-chain variable region CDR2 having an amino acid sequence set forth in SEQ ID NO: 7, and vi) a light-chain variable region CDR3 having an amino acid sequence set forth in SEQ ID NO: 8. An object of the method according to one exemplary embodiment of the present invention is to exactly measure an amount of a test substance to be measured using an antigen-antibody reaction.

According to one exemplary embodiment of the present invention, errors in analysis, especially, quantitative analysis, may be minimized by reflecting errors in a test zone, which occur by factors such as temperatures of a sample and a device, an amount and components of an injected sample, variations of the device, and the like, in a reference zone, for example, by maintaining a ratio of a signal intensity value in the test zone/a signal intensity value in the reference zone (hereinafter referred to as a T/R ratio) constant. Specifically, the numerical values measured even in the sample from the same human may be differently expressed by the factors such as differences in viscosity and components caused by large amounts of materials present in the sample, non-specific reactions, an amount of the sample upon injection of the sample, and an environment in which the sample is measured. In this case, the method for the immunological measurement according to one exemplary embodiment of the present invention makes the T/R ratio constant by reflecting the numerical values in the test zone changed by the effect of external factors, in the numerical values in the reference zone.

According to one exemplary embodiment of the present invention, since reference antibodies having similar antigen-antibody binding characteristics to the temperature-dependent antigen-antibody binding characteristics in the test zone may be freely selected by user's convenience, it is possible to compose a reference antibody suitable for a diseases to be diagnosed.

In the present invention, the hapten is a low-molecular organic compound which itself cannot induce an immune response but induces an immune response only when the hapten is attached to a carrier molecule. In the present invention, atrazine (chemical name: 2-chloro-4-(ethylamino)-6-(isopropylamino)-s-triazine), or a derivative thereof widely used as a herbicide may be used as the hapten.

For example, the derivative of atrazine may include propazine, prometryn, prometon, simazine, simetryn, ipazine, trietazine, cyanazine, or a derivative thereof.

In the present invention, by way of example, atrazine may be used as the hapten, and an antibody binding to atrazine may be developed and used as a reference antibody. As a result, the atrazine and the antibody may be used for exact quantitative measurement of the sample.

In the present invention, the antibody binding to the hapten may be prepared according to a conventional method for preparing an antibody, and concentration and purification methods such as ultrafiltration, ammonium sulfate fractionation, ion exchange chromatography, gel filtration chromatography, and affinity chromatography may be properly combined and used to prepare the antibody.

According to one exemplary embodiment of the present invention, the antibody may be prepared by developing a variety of antibodies specifically binding to atrazine using a phage display and constructing a library of antibodies having different affinity constants and various antigen binding affinities according to the temperature. In this case, the antibody may be used as the hapten antibody. Therefore, in the present invention, the reference antibody having similar reactivity characteristics to the temperature-dependent antigen-antibody binding characteristics in the test zone may be selected and used upon the actual measurement of the sample.

In the present invention, the hapten antibody may include a heavy-chain variable region having an amino acid sequence set forth in SEQ ID NO: 1; and a light-chain variable region having an amino acid sequence set forth in SEQ ID NO: 2.

In the present invention, the method for the immunological measurement using the reference antibody may be performed by reactions in (1) a conjugate zone in which a probe (i.e., a test probe) specifically binding to a test substance in a sample, and a probe (i.e., a reference probe) specifically binding to a hapten or hapten antibody are impregnated together; (2) a test zone in which an antibody (hereinafter referred to as a capture antibody) specifically binding to the test substance is impregnated; and (3) a reference zone in which the hapten or hapten antibody is impregnated.

In the present invention, the probe specific to the test substance in the sample, and the probe specific to the hapten are mixed and impregnated in the conjugate zone. When the sample is injected through a sample injection port, the test substance in the sample binds to the probe specific to the test substance to form a complex. The complex spreads to the test zone and the reference zone along a spreading membrane.

The test substance to be analyzed in the sample may include organic substances derived from all kinds of mammals, or artificially synthesized organic molecules. For example, the test substance may include drugs, toxins, proteins, carbohydrates, nucleic acids, and the like, but the present invention is not limited thereto. According to one exemplary embodiment of the present invention, the test substance may be a thyroid-stimulating hormone (TSH), a prostate-specific antigen (PSA), an α-fetoprotein (AFP), a creatine phosphokinase (CK-MB), troponin I (TnI), myoglobin, a high-sensitivity C-reactive protein (hsCRP), a D-dimer, a luteinizing hormone (i.e., testosteron), or vitamin D.

Also, the sample including the test substance may be in the form of blood, a serum, plasma, urine, tear, saliva, breast milk, or a cell culture supernatant.

The probe is used for the purpose of measuring and searching for a target object, and directly or indirectly generates recognizable or detectable signals by means of fluorescence when a specific binding reaction occurs. The signals detectable of the probe include spectrophotometric signals, visible signals, electrochemical signals, and other electrically detectable signals.

In the present invention, the test zone is a zone in which a capture antibody against the test substance is impregnated. The test substance in the sample binds to the capture antibody in the test zone. Specifically, the complex obtained in the conjugate zone may emit signals, when the complex binds to the capture antibody against the test substance impregnated in the test zone. For example, the complex of the probe and TSH obtained in the conjugate zone may bind to an anti-TSH antibody impregnated in the test zone, and the probe emit signals, for example light, by means of the binding reaction of the complex to the anti-TSH antibody.

In the present invention, the reference zone has a hapten or hapten antibody impregnated therein. For example, (1) when the hapten is impregnated in the reference zone, the complex formed by binding the hapten antibody to the probe specific to the hapten antibody in the conjugate zone binds to the hapten so that the probe can emit light, or (2) when the hapten antibody is impregnated in the reference zone, the complex formed when the hapten binds to the probe specific to the hapten may emit signals as the complex binds to the hapten antibody so that the probe can emit light.

Each of the conjugate zone, the test zone and the reference zone may also contain a reagent.

According to one exemplary embodiment of the present invention, the method for the immunological measurement of the present invention may use a microchip provided with a micro-channel which accommodates a sample to be analyzed and in which a reaction occurs, and a conjugate zone, a test zone, a reference zone and a reaction termination zone may be sequentially present in the micro-channel present in a bottom plate of the microchip. A probe specifically binding to a reagent and an antigen (for example, TSH) to be detected; and a probe specifically binding to a hapten or hapten antibody may be fixed in a surface of the conjugate zone, and a capture antibody specifically binding to the reagent and an antigen (for example, TSH) to be detected may be fixed in a surface of the test zone. Also, the reagent and the hapten or hapten antibody may be fixed in a surface of the reference zone.

After the sample to be analyzed is dropped into the micro-channel through a sample injection port, the microchip is mounted on an analyzer (for example, an automated immunoassay system), and then a cross section of the micro-channel is exposed to an optical sensor of the analyzer to convert fluorescent signals into electrical signals. Subsequently, the presence of a detectable antigen and the amount of the sample to be analyzed may be automatically determined using a method of calculating signals in each zone.

More specifically, the method for the immunological measurement using the reference antibody including a hapten and an antibody binding to the hapten according to one exemplary embodiment of the present invention may include (1) injecting a sample into a micro-channel through a sample injection port; (2) allowing a test substance in the sample to bind to a probe specific to the test substance in a conjugate zone to form a test substance-probe complex and allowing a hapten or hapten antibody to bind to a probe specific to the hapten or hapten antibody to form a hapten- or hapten antibody-probe complex; (3) spreading the complex to a test zone and a reference zone along a spreading membrane; (4) allowing a capture antibody against the test substance to bind to the test substance-probe complex in the test zone; (5) allowing the hapten- or hapten antibody-probe complex to bind to the hapten or hapten antibody in the reference zone; (6) measuring signals; and (7) analyzing the signals.

Also, the present invention provides a device for the immunological measurement using a reference antibody, which is characterized by including a hapten and an antibody binding to the hapten. Here, the antibody includes i) a heavy-chain variable region CDR1 having an amino acid sequence set forth in SEQ ID NO: 3, ii) a heavy-chain variable region CDR2 having an amino acid sequence set in SEQ ID NO: 4, iii) a heavy-chain variable region CDR3 having an amino acid sequence set in SEQ ID NO: 5; iv) a light-chain variable region CDR1 having an amino acid sequence set in SEQ ID NO: 6, v) a light-chain variable region CDR2 having an amino acid sequence set in SEQ ID NO: 7, and vi) a light-chain variable region CDR3 having an amino acid sequence set in SEQ ID NO: 8.

The hapten, the hapten antibody binding to the hapten, and the reference antibody are as described above.

In the present invention, the device for the immunological measurement is characterized in that it uses a capillary force, a micro-channel, chromatography, or a nitrocellulose membrane.

According to one exemplary embodiment of the present invention, the device for the immunological measurement may use a microchip provided with a micro-channel including a reference antibody (i.e., a hapten antibody), and the micro-channel may include (1) a conjugate zone in which a test probe specifically binding to a test substance in a sample, and a reference probe specifically binding to a hapten or hapten antibody are impregnated together; (2) a test zone in which a capture antibody specifically binding to the test substance is impregnated; and (3) a reference zone in which the hapten or hapten antibody is impregnated.

In this specification, the term "antibody" refers to a substance produced by stimulation of an antigen in the immune system, but the types of the antibody are not particularly limited. In this specification, the antibody encompasses all types of animal antibodies, chimeric antibodies, humanized antibodies, or fully human antibodies. In this specification, the antibody also includes fragments of antibodies having an antigen-binding activity, for example, Fab.

EXAMPLES

Hereinafter, the present invention will be described in further detail with reference to the following Examples. However, it should be understood that the following Examples are given by way of illustration of the present invention only, and are not intended to limit the scope of the present invention.

Example 1: Animal Immunized by Atrazine-Carrier

In the present invention, various antibodies against atrazine (Biocell) as a hapten were developed, and a library of antibodies having different affinity constants and various antigen binding affinities according to the temperature was constructed. The here are no antibodies present in the human body, since the hapten was not present in the human body and did not cause an immune response.

To screen antibodies specifically binding to atrazine, first of all, a library of animal-immunized antibodies was constructed. The library was constructed by immunizing an animal with an atrazine-carrier protein (keyhole limpet hemocyanin (KLH) or ovalbumin (OVA)), obtaining mRNAs from immune cells, amplifying an antibody gene by means of PCR using a primer combination of the antibody gene, and cloning the antibody gene into a vector for phage display.

Specifically, 100 μg of atrazine-KLH or atrazine-OVA (BioSell, US) was mixed with a complete Freund's adjuvant and an incomplete Freund's adjuvant (Sigma, US) at a ratio of 1:1, and the resulting mixtures were alternately subcutaneously injected into three white leghorn chickens four times at a dose of 0.5 ml per head and an interval of 3 weeks.

Sera were obtained from the immunized animals, diluted with PBSB (PBS supplemented with 3% BSA) to concentrations of 1:100, 1:500, 1:2,500, 1:12,500, and 1:62,500, and stored. Then, the binding of atrazine-BSA, which was not used for immunization, to atrazine was determined using an enzyme-linked immunosorbent assay (ELISA). This method was as follows: 1 μg/ml of atrazine-BSA was added to an ELISA plate, and coated overnight at 4° C., and the diluted sera were then added, and reacted at 37° C. for 2 hours. The resulting reaction solution was washed three times with PBST (PBS supplemented with 0.1% Tween 20), and an anti-chicken immunoglobulin-horseradish peroxidase (HRP) was diluted at 1:2,000, added, and reacted for an hour. The reaction solution was washed three times with PBST, and 50 μL of ABTS (Thermo, US) was added thereto, and reacted for 20 minutes to develop a color. Then, the reaction solution was measured for absorbance at 405 nm using a microplate reader. The animals producing the sera more strongly binding to atrazine-BSA after immunization than the sera before the immunization were selected.

Example 2: Construction of Antibody Library (2-1) cDNA Synthesis

Tissues were obtained from the bone marrows, spleens, and bursae of Fabricius of the selected chickens after 5 days of the last subcutaneous injection in Example 1. The tissues obtained above were mixed with 10 ml of Trizol (Invitrogen, US), and homogenized with a homogenizer. Then, 20 ml of Trizol was further added, and the resulting mixture was centrifuged at 3,500 rpm for 10 minutes to obtain a supernatant. 3 ml of 1-bromo-3-chloropropane (BCP, Sigma, US) was added to the supernatant, and then centrifuged to obtain a supernatant. 15 ml of isopropanol was added to the supernatant, and total RNAs were precipitated, and obtained by centrifugation.

The total RNAs obtained above were subjected to a reverse transcription reaction (at 65° C. for 5 minutes, at 4° C. for 5 minutes, at 50° C. for 50 minutes, and at 85° C. for 5 minutes) using Oligo dT as a primer, and a SuperScript transcription system (Invitrogen, US). 2 μl of a reaction solution including cDNAs which were reaction products of the reverse transcription reaction was loaded in 1% agarose gel, and electrophoresed to determine cDNA bands having various lengths.

(2-2) Amplification of Antibody Gene

To amplify variable regions $V_H$ and $V_L$ of the heavy and light chains of the chicken antibodies from the cDNA obtained in Example 2-1, a PCR reaction was performed, as follows. The PCR reaction was first performed using the cDNA synthesized in Example 2-1 as a template to amplify $V_H$ and $V_L$ domains, and each of the amplified $V_H$ and $V_L$ domains was purified. Then, the $V_H$ and $V_L$ domains were ligated by means of PCR to construct a single-chain FV (scFv) fragment.

Specifically, 0.5 μl of the cDNA library obtained in Example 2-1, 30 pmole of each of forward and reverse primers (SEQ ID NOS: 9 and 10, and SEQ ID NOS: 11 and 12) for the $V_H$ and $V_L$ domains listed in the following Table 1, a 10×PCR buffer, 200 uM dNTPs and 0.5 μl of a Taq DNA polymerase were mixed to a final volume of 50 μl, and reacted at 94° C. for 5 minutes. Thereafter, the resulting reaction solution was subjected to PCR which was repeatedly performed for 30 cycles at 94° C. for 15 seconds, at 56° C. for 30 seconds, and at 72° C. or 90 seconds. Subsequently, the PCR-amplified antibody DNAs were electrophoresed in 1% agarose gel, isolated according to the size of the amplified DNAs, and purified using a gel extraction kit (Elpis Biotech Inc., Korea).

Meanwhile, to obtain scFv DNAs, 50 ng of the purified $V_H$ domain and 50 ng of the purified $V_L$ domain were used as the templates, and 30 pmole of scFv forward and reverse primers (SEQ ID NO: 13 and 14) listed in the following Table 1, a 10×PCR buffer, 200 uM dNTPs and 0.5 μl of a Taq DNA polymerase were mixed to a final volume of 50 μl, and then reacted at 94° C. for 5 minutes. Thereafter, the resulting reaction solution was subjected to PCR which was repeatedly performed for 20 cycles at 94° C. for 30 seconds, at 56° C. for 30 seconds, and at 72° C. for 2 minutes. Subsequently, the PCR-amplified antibody DNAs were electrophoresed in 1% agarose gel, isolated according to the size of each of the amplified DNAs, and purified using a gel extraction kit (Elpis Biotech Inc., Korea).

TABLE 1

Primers used in PCR reaction

| Items | Primer | Sequence | SEQ ID NO |
|---|---|---|---|
| $V_H$ | Forward | GGT CAG TCC TCT AGA TCT TCC GGC GGT GGT GGC AGC TCC GGT GGT GGC GGT TCC GCC GTG ACG TTG GAC GAG | 9 |
|  | Reverse | CTG GCC GGC CTG GCC ACT AGT GGA GGA GAC GAT GAC TTC GGT CC | 10 |
| $V_L$ | Forward | GTG GCC CAG GCG GCC CTG ACT CAG CCG TCC TCG GTG TC | 11 |
|  | Reverse | GGA AGA TCT AGA GGA CTG ACC TAG GAC GGT CAG G | 12 |
| scFv | Forward | GAG GAG GAG GAG GAG GAG GTG GCC CAG GCG GCC CTG ACT CAG | 13 |
|  | Reverse | GAG GAG GAG GAG GAG GAG GAG CTG GCC GGC CTG GCC ACT AGT GGA GG | 14 |

(2-3) Construction of Antibody Library

The scFv DNA prepared in Example 2-2, and a phagemid vector, pComb3X (the Scripps Research Institute, US), were digested with a restriction enzyme SfiI (Roche, US).

Specifically, 10 μg of a PCR fragment encoding the scFv prepared in Example 2-2, 360 units of SfiI, and 20 μl of a 10× buffer were added to a final volume of 200 μl, and reacts overnight at 50° C. Also, 20 μg of a pComb3X vector, 120 units of SfiI, and 20 μl of a 10× buffer were added, to a final volume of 200 μl, and reacted overnight at 50° C. The respective fragments digested with the restriction enzyme as described above were electrophoresed in 1% agarose gel, and then purified using a gel extraction kit (Elpis Biotech Inc., Korea).

To insert the scFv fragment into the pComb3X vector, 700 ng of the scFv fragment digested with the restriction enzyme SfiI as described above, and 1.4 µg of a pComb3X vector were mixed, and a T4 DNA ligase (Invitrogen, US) was added thereto, and reacted overnight at 16° C. The ligation mixture was purified by means of an ethanol precipitation method using 2× volume of ethanol and 0.3M sodium acetate, and transformed into *Escherichia coli* ER2738 (New England Biolab, US) by means of electroporation. The transformed *E. coli* was cultured in the presence of 50 µg/ml carbenicillin and 70 µg/ml kanamycin to construct a library with $1 \times 10^9$ complexities.

Example 3: Screening of Anti-Atrazine Antibody

Antibodies binding to atrazine were screened from the library of antibodies, which had heavy chains and light chains randomized in the form of scFv obtained in Example 2, using atrazine-BSA supported by a solid.

(3-1) Screening of Phage Including scFv Binding to Atrazine

First of all, 3 µg of atrazine-BSA was conjugated with magnetic beads.

Also, 100 µg/ml of carbenicillin, 70 µg/ml of kanamycin, and a VCSM13 helper phage (1:1,000: Stratagene, US) were added to *E. coli* including the library constructed in Example 2-3, and reacted overnight at 37° C. to induce growth of the phage in which the antibody was expressed. The *E. coli* culture broth was centrifuged to recover only a supernatant, and 40 mg/ml of polyethylene glycol 8000 and 30 mg/ml of NaCl were added thereto, and centrifuged to collect the precipitated phage, which was re-suspended with PBS.

The phage expressing the antibody library obtained above, and the atrazine-BSA conjugated with the magnetic beads were reacted at room temperature for 2 hours to bind the phase having an affinity to atrazine. The phase bound to atrazine was washed with PBS supplemented with 0.5% Tween 20, eluted with a 0.1 M glycine (pH 2.2) solution, and neutralized with a 1 M Tris (pH 9.0) solution (panning) *E. coli* ER2738 was infected with the eluted phage for next-round panning, cultured overnight for growth, and recovered with 40 mg/ml polyethylene glycol 8000 and 30 mg/ml NaCl. In this way, the panning was repeatedly performed four times, and the washing number increased with an increasing panning number to accumulate the phage having a high binding affinity.

Respective clones screened from a plate of the tertiary and quaternary panned products were put into a 96-deep well plate, and 100 µg/ml of carbenicillin, 70 µg/ml of kanamycin, and VCSM13 helper phage (1:1000) were also added thereto, and cultured overnight at 37° C. to induce growth of the phage in which the antibody was expressed. A culture broth including the phage was obtained, and then subjected to an enzyme-linked immunosorbent assay (ELISA) using atrazine-BSA to determine the presence of the phage including antibody clones binding to atrazine. In the method, 1 µg/ml of atrazine-BSA was put into an ELISA plate, coated overnight at 4° C., and then washed three times with PBST (PBS supplemented with 0.1% Tween 20). Subsequently, the resulting mixture was reacted at 37° C. for an hour in PBS supplemented with 1% BSA (Sigma, US), and the culture broth including the phage obtained above was added thereto, and reacted at 37° C. for 2 hours. The resulting reaction mixture was washed three times with PBST, and anti-HA (a hemagglutinin tag bound to scFv) conjugated with HRP was diluted at 1:2,000, and reacted for an hour. The reaction mixture was washed three times with PBST, and 100 µL of ABTS was added thereto, and reacted to develop a color. Then, the reaction solution was measured for absorbance at 405 nm using a microplate reader. The phages including the antibody clones showing positive signals for atrazine-BSA were selected.

(3-2) Sequencing of Screened Antibodies

ER2738 *E. coli* including the clones showing the positive signal for atrazine as screened in Example 3-1 were cultured overnight in an SB medium (30 g/L of tryptone, 20 g/L of a yeast extract, and 10 g/L of MOPS, pH 7.0), and then centrifuged to obtain transformed *E. coli*. Plasmid DNAs were obtained from the transformed *E. coli* using a DNA mini-prep kit (GeneAll Biotechnology Co., Ltd., Korea), and then sequenced.

For the sequencing, the plasmid DNAs were sequenced using ScFv sequencing primers as listed in the following Table 2, and the screened antibodies were designated by numbers. Also, specific information on amino acid sequences of heavy-chain and light-chain CDRs of the #1 antibody of antibodies used in this experiment is listed in the following Table 3.

TABLE 2

| scFv sequencing primers | | |
|---|---|---|
| | Sequence | SEQ ID NO |
| Forward | ACA CTT TAT GCT TCC GGC TC | 15 |
| Reverse | CAA AAT CAC CGG AAC CAG AG | 16 |

TABLE 3

Amino acid sequences of heavy-chain and light-chain CDRs of one antibody used in this experiment

| | Sequence | SEQ ID NO |
|---|---|---|
| HCDR1 | GFSIGDYGMG | 3 |
| HCDR2 | SIRSDGSSTYYGSAVKG | 4 |
| HCDR3 | DGVGWSATIDA | 5 |
| LCDR1 | SGGGGSYG | 6 |
| LCDR2 | YNNKRPS | 7 |
| LCDR3 | GSTDIRSTPI | 8 |

Example 4: Production of Antibodies

To analyze the affinity and characteristics of the antibodies screened above, a chimeric antibody in which a chicken variable region and a mouse constant region ($C_H$ and $C_k$ of an IgG2a subtype) were bound to each other was produced in the form of IgG.

First, a fragment of the variable region was obtained from the pComb3x plasmid including the scFv gene, which was obtained for scFv sequencing as described above, by means of PCR. In this case, fragments of the variable regions from the heavy and light chains were obtained, respectively, using a pair of primers set forth in SEQ ID NOS: 17 and 18 and a pair of primers set forth in SEQ ID NO: 23 and 24, as listed in the following Table 4.

The fragments $C_H$ and $C_k$ of the constant region were obtained by means of PCR using a plasmid including $C_H$ and $C_k$ of mouse IgG2a as a template. In this case, the $C_H$ and $C_k$ were obtained, respectively, using a pair of primers set forth in SEQ ID NOS: 19 and 20, and a pair of primers set forth in SEQ ID NOS: 25 and 26, as listed in the following Table 4.

The variable and constant regions obtained above were subjected to PCR using a pair of primers set forth in SEQ ID NOS: 21 and 22, and a pair of primers set forth in SEQ ID NOS: 23 and 24, as listed in the following Table 4, thereby obtaining a heavy-chain fragment (HC) and a light-chain fragment (LC), respectively. In this case, the PCR was performed under the same conditions as described in Example 2.

The heavy-chain and light-chain DNAs of the antibody obtained above were transferred to mammalian cell expression plasmids, respectively, using a pcDNA3.3™-TOPO®TA cloning kit and a pOPTIVEC™-TOPO®TA cloning kit (Invitrogen, US). That is, the heavy-chain and light-chain DNAs were mixed respectively with 1 µl of a pcDNA3.3™-TOPO® vector and a pOPTIVEC™-TOPO® vector, and the resulting mixtures were added to a buffer supplemented with 200 mM NaCl and 10 mM MgCl$_2$ to a total volume of 6 µl, and then reacted at room temperature for 5 minutes to be ligated. Heat shock was applied to E. coli DH5α competent cells to transform the competent cells with the ligated product, and the competent cells were cultured to obtain colonies. The colonies were cultured in a large scale in an SB medium to obtain a plasmid.

HEK293F cells (Invitrogen, US) were transfected with the plasmid prepared above, and then cultured for 7 days under conditions of 135 rpm and 8% CO$_2$ to obtain a culture broth. The antibodies in the culture broth were purified using a protein A column (GE, US). The culture broth was loaded in the column to bind the antibody (IgG) in the culture broth to protein A, and the antibody (IgG) bound to the protein A was eluted with a 20 mM sodium citrate buffer (pH 3.0), and then neutralized with a phosphate buffer. Thereafter, the eluted antibody (IgG) was subjected to SDS-PAGE to determine whether the molecular weights of the heavy and light chains were consistent with theoretical values, and the purified proteins were obtained with high purity.

TABLE 4

| Items | Primer | Sequence | SEQ ID NO |
|---|---|---|---|
| $V_H$ | Forward | GCT AGC CGC CAC CAT GGG CTG GTC CTG CAT CAT CCT GTT CCT GGT GGC CAC CGC CAC CGG CGC CGT GAC GTT GGA CGA GTC CGG G | 17 |
| | Reverse | AGA TGG TGC GGT AGT TTT AGC GGA GGA GAC GAT GAC TTC | 18 |
| $C_H$ | Forward | GCT AAA ACT ACC GCA CCA TCT | 19 |
| | Reverse | GGA TCC CTT GCC GGC CGT CGC | 20 |
| HC | Forward | CTA GCT AGC CGC CAC CAT GGG | 21 |
| | Reverse | GAC ACC TAC TCA GAC AAT GC | 22 |

TABLE 4-continued

| Items | Primer | Sequence | SEQ ID NO |
|---|---|---|---|
| $V_L$ | Forward | AAG CTT GCC GCC ACC ATG GGC TGG TCC TGC ATC ATC CTG TTC CTG GTG GCC ACC GCC ACC GGC GCC CTG ACT CAG CCG TCC TCG GTG | 23 |
| | Reverse | CAC GGT TGG GGC TGC ATC GGC TAG GAC GGT CAG GGT TGT | 24 |
| $C_k$ | Forward | GCC GAT GCA GCC CCA ACC GTG | 25 |
| | Reverse | TCT AGA CTA ACA CTC ATT TCT GTT | 26 |
| LC | Forward | CCC AAG CTT GCC GCC ACC ATG | 27 |
| | Reverse | GGA CAC CTA GTC AGA CAA AAT G | 28 |

Example 5: Affinity Analysis

The affinity of the antibody screened in Example 4 to atrazine was analyzed using ELISA and surface plasmon resonance (SPR).

To analyze the affinity of the antibody using ELISA, first of all, 1 µg/ml of atrazine-BSA was added to a 96-well immunoplate (Corning, US), stored overnight at 4° C. to coat the bottom of the plate with the atrazine-BSA, and then washed three times with PBST (PBS supplemented with 0.1% Tween 20). Thereafter, the immunoplate was reacted at 37° C. for an hour in PBS supplemented with 1% BSA (Sigma, US), washed three times with PBST, and treated with antibodies, which were diluted at an increasing concentration (0.001, 0.003, 0.01, 0.03, 0.1, 0.3, 1, 3, 10, 30 and 100 nM), at a dose of 50 µL per well for each antibody. The immunoplate was reacted at 37° C. for an hour to bind the antibody to the antigen, and then washed three times with PBST. Anti-mouse immunoglobulin Fc-HRP (Jackson, US) was diluted at 1:2000, treated at a dose of 50 µL per well, and then reacted at room temperature for an hour. When the reaction was completed, the immunoplate was washed three times with PBST, and 50 µL of ABTS was added to each well, and reacted for 20 minutes to develop a color. Then, the reaction solution was measured for absorbance at 405 nm using a microplate reader (Biotek, USA). The results are shown in FIG. 2.

Figure 2:
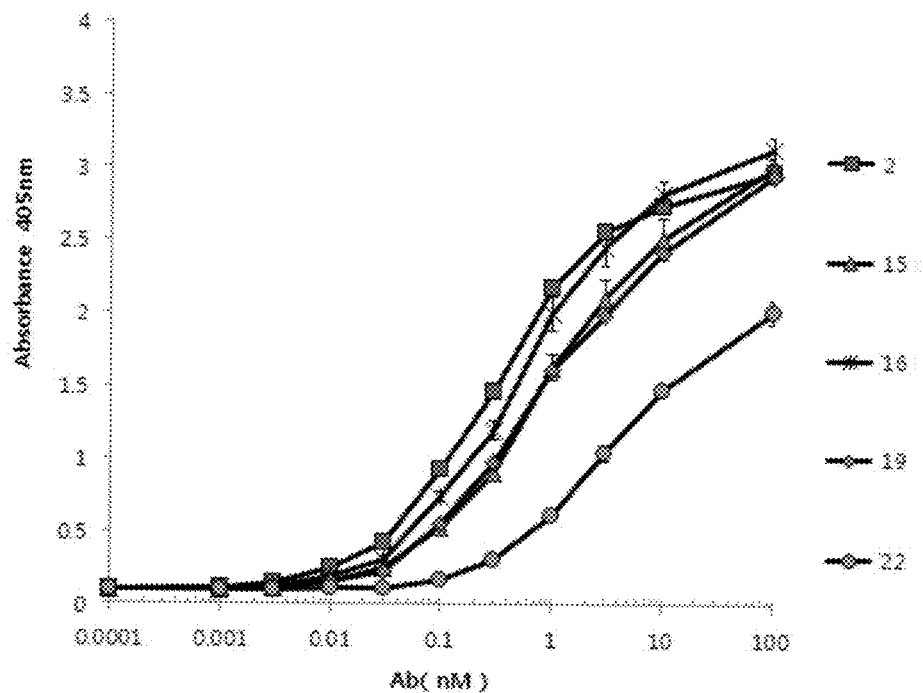
FIG. 2 shows the results (ELISA) obtained by analyzing the affinity of an antibody against atrazine.
Figure 2:
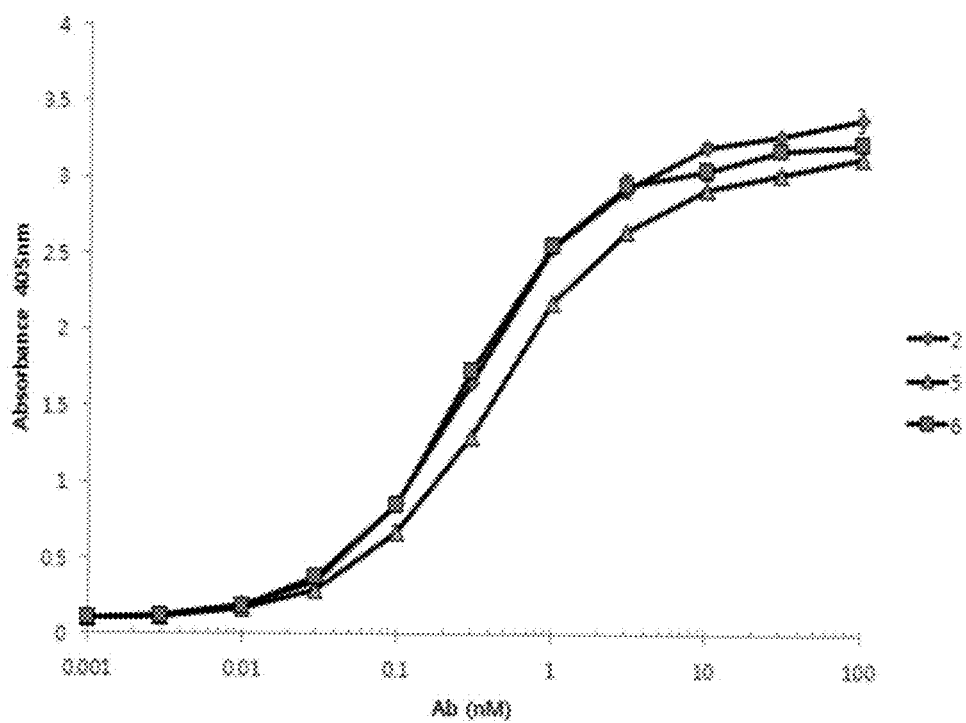
Figure 2:
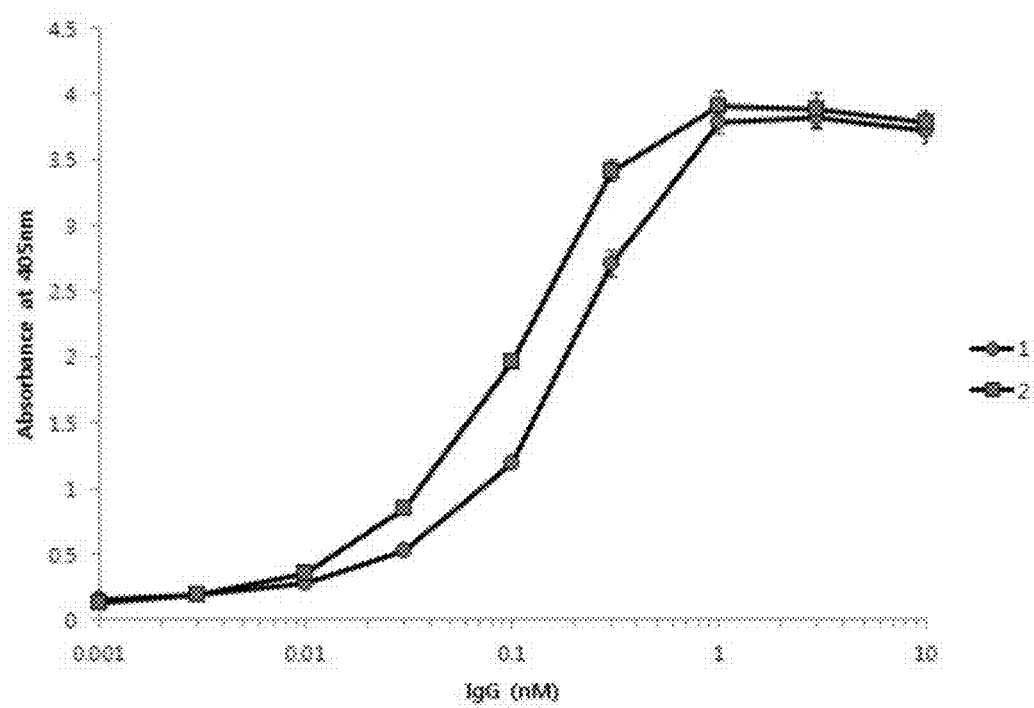
Figure 2:
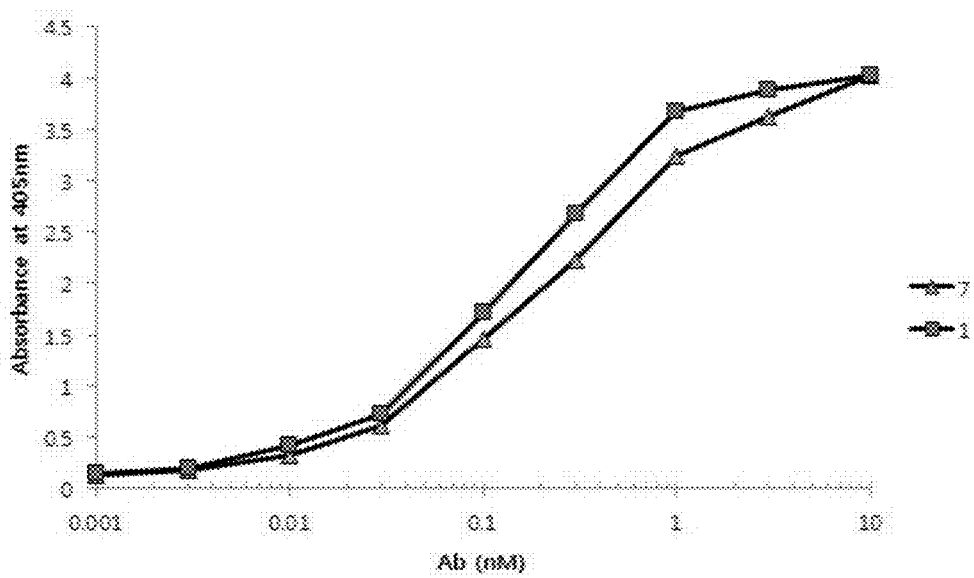

As shown in FIG. 2, the result of analysis of the affinity of the antibody against atrazine showed that the screened antibody clones were bound to atrazine with high affinity.

Meanwhile, to analyze the affinity of the screened antibody to atrazine using SPR as another method, atrazine-BSA was coupled to a carboxymethylated dextran biosensor chip (CM5, GE, US) according to the manufacturer's instruction. To measure association/dissociation rates, a chip having atrazine-BSA coupled thereto was mounted in Biacore® (GE, US) equipment, and an antibody protein of each clone continued to be doubly diluted to concentrations of 50 nM, 25 nM, 12.5 nM, 6.25 nM, 3.13 nM and 1.56 nM, and injected thereto. The association and dissociation of the antibody to/from atrazine were represented by sensogram, an association rate constant and a dissociation rate constant were calculated using a simple 1:1 Langmuir binding model (BIAcore X100 Evaluation Software, Version 2.0). The equilibrium dissociation constant (KD) was a value obtained by dividing the dissociation rate constant (Kd) by the association rate constant (Ka). When the equilibrium dissociation constant (KD) was calculated as an actual value, it was confirmed that the antibody had a high KD value less than or equal to nM.

Figure 3:
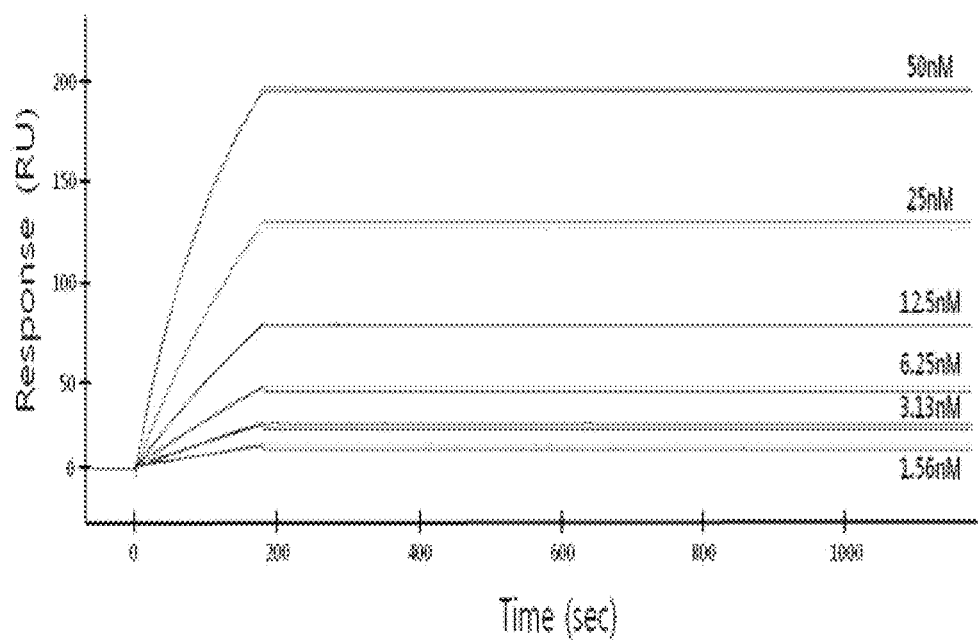
FIG. 3 shows the surface plasmon resonance (SPR) sensogram results of a #2 antibody among anti-atrazine antibodies according to one exemplary embodiment of the present invention.

The SPR sensogram results of the clones are shown in FIG. 3. As a result, it could be seen the antibody clones had high $K_{on}$ and $K_{off}$ values, and were rapidly associated to atrazine and slowly dissociated from atrazine.

Example 6: Analysis of Chemicophysical Characteristics

The chemicophysical characteristics of the screened antibodies were analyzed.

Antibody proteins were prepared under (1) a reducing condition (R) in which dithiothreitol (DTT) was treated to remove disulfide bonds and (2) a non-reducing condition (NR) in which DTT was not treated, and then subjected to SDS-polyacrylamide gel electrophoresis (SDS-PAGE) using a NuPAGE 4-12% Bis-Tris gel (Invitrogen, US). The proteins separated on the gel by an electrical force according to the molecular weight were stained with a Coomassie solution (0.1% Coomassie, 45% methanol, 10% acetic acid). The molecular weights of the heavy chains, and the light chains of the 11 antibody types screened in the present invention, and the bridged forms thereof were measured. The results are shown in FIG. 4.

Figure 4:
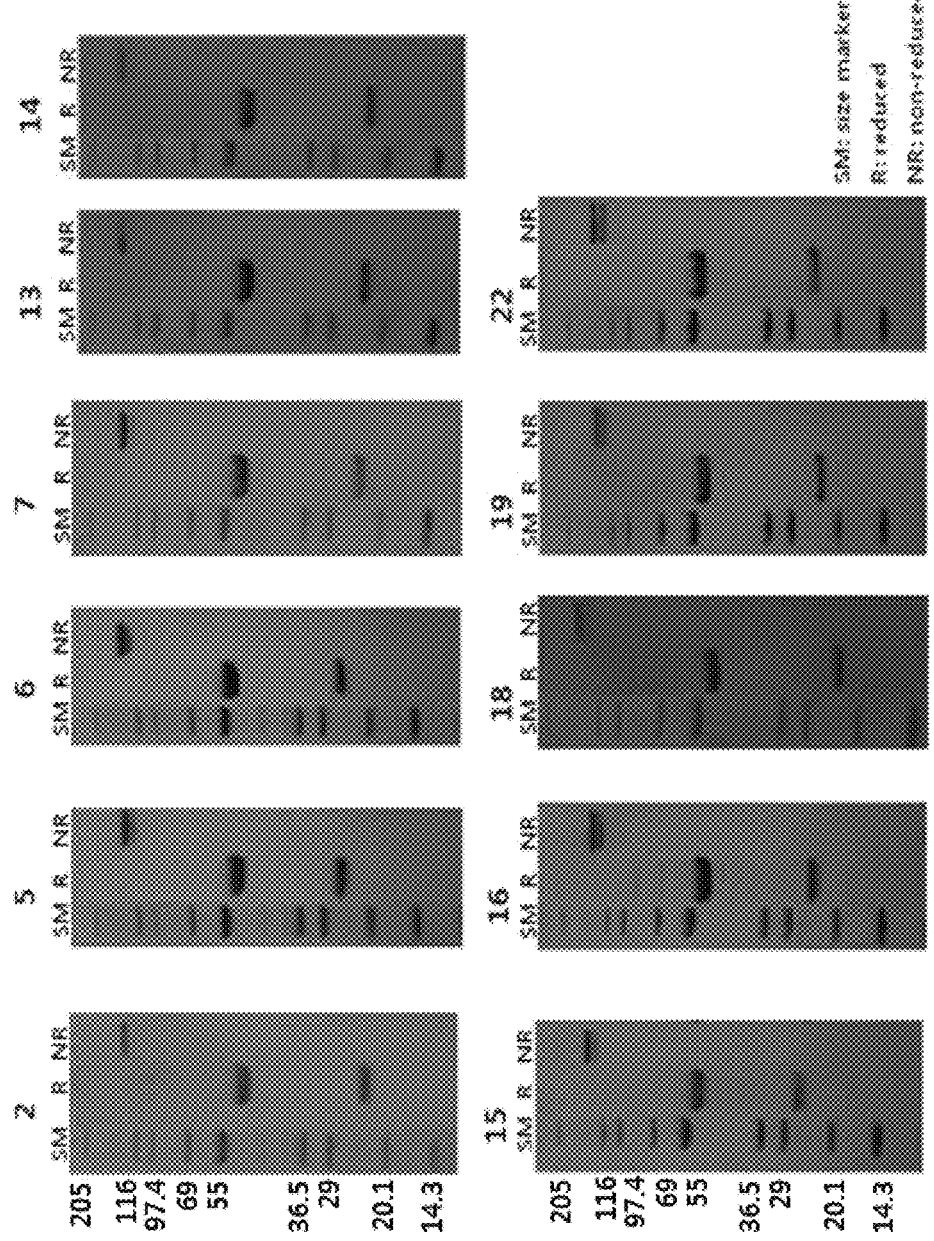
FIG. 4 shows the SDS-PAGE result of the anti-atrazine antibodies according to one exemplary embodiment of the present invention, where SM represents a size marker, and R and NR represent reducing and non-reducing conditions, respectively.

As shown in FIG. 4, it was revealed that, when the heavy and light chains of the antibodies were analyzed under the reducing condition (R), one major band was observed in the vicinity of each of 55 kDa and 20.1 kDa size markers, indicating that the major bands corresponded to the heavy chains and the light chains of the antibodies. In the case of the specimen analyzed under the non-reducing condition, one major band was observed between a 116 kDa size marker and a 205 kDa size marker, indicating that the heavy and light chains were bridged in the antibodies. Also, since other bands rather than the bands corresponding to the heavy and light chains of the antibodies, and the bridged forms thereof were not observed, the purified proteins were expected to have a purity of 90% or more.

As a kind of analysis of purity of the purified antibody protein, a level of soluble aggregate was also analyzed by size exclusion chromatography-high performance liquid chromatography (SE-HPLC) using a TSK gel G3000SWx1 column (Tosoh, Japan). The antibody protein was isolated by an isocratic elution method using a 100 mM phosphate buffer (pH6.6) as a mobile phase, and monitored for an absorbance at 280 nm. In this case, the ratio of an area of peaks of monomers to the total area of peaks was 96% in average, indicating the antibody proteins showed high purity. Also, the ratios of the peaks of the aggregates were proven to be 0% (four aggregates), 4 to 8% (four aggregates), and 12.8% (one aggregate).

Experimental Example 1

Correction of Difference in Result Values Caused Due to Difference in Viscosity of Sample Test serum samples from patients applied to the Department of Laboratory Medicine, College of Medicine, Kangwon National University were used as the blood samples used in the present invention, and a group of patients were selected in a random manner. The group of patients included thyroid disease patients, and a thyroid-specific antigen (i.e., a thyroid stimulating hormone (TSH)) was used as a biomarker. The amount of TSH present in the sera of the patients was measured using an automated immunoassay system (Access 2 analyzer, Beckman Coulter). Among these, the three samples having the same concentration but different viscosities were selected, and measured for TSH concentration using the device for the immunological measurement according to one exemplary embodiment of the present invention.

Specifically, the respective test serum samples 1 to 3 were dropped at a dose of 30 μL through a sample injection port of a microchip, and the microchip was inserted into the measurement device after the lapse of 5 minutes. The measurement device was a microchip provided with a micro-channel which accommodated a sample to be analyzed and in which a reaction occurred, and was manufactured so that a conjugate zone, a test zone, a reference zone, and a reaction termination zone were sequentially present in a bottom plate of the microchip. A probe specifically binding to TSH; and a probe specifically binding to atrazine or an atrazine antibody were fixed in a surface of the conjugate zone. A capture antibody specifically binding to the reagent and TSH was fixed in a surface of the test zone. Also, the reagent, and the atrazine or atrazine antibody was fixed in a surface of the reference zone.

When the sample to be analyzed was dropped into the micro-channel through a sample injection port, and the microchip was mounted on a measurement device, a cross section of the micro-channel was exposed to an optical sensor of the analyzer to convert fluorescent signals into electrical signals. Subsequently, the presence of a detectable antigen and the amount of TSH may be automatically determined using a method of calculating signals in each zone.

After approximately 40 seconds when the microchip was inserted into the measurement device, the (quantitative) amount of TSH in the sample and the signal intensity values in the test zone and the reference zone were displayed on a display screen of the measurement device. The fluorescent signal in the test zone and the fluorescent signal in the reference zone were measured by the following Equations 1 and 2, respectively, and the ratio of the fluorescent signals between the test zone and the reference zone was calculated. The results are listed in the following Table 5.

Fluorescent signal in test zone=$\int_{Xtc-30}^{Xtc+30}(Xn-Xb)$  [Equation 1]

Fluorescent signal in reference zone=$\int_{Xrc-30}^{Xrc+30}(Xn-Xb)$  [Equation 2]

In Equations 1 and 2,

Xn represents a fluorescent signal at an $n^{th}$ position;

Xtc represents a fluorescent signal in the center of the test zone;

Xrc represents a fluorescent signal in the center of the reference zone; and

Xb represents an average value of fluorescent signals in at least 50 points at position of micro-channels 0-900, where 0-900 represents the numbered sections in which a signal measurement zone in the micro-channel is divided at constant intervals.

TABLE 5

|  | Test zone | Reference zone | Ratio (T/R) |
| --- | --- | --- | --- |
| Sample 1 | 60431 | 43987 | 1.374 |
| Sample 2 | 54177 | 41354 | 1.310 |
| Sample 3 | 35724 | 26763 | 1.335 |

Considering the signals in the test zone, it was confirmed that the sample 1 had the highest signal intensity, and a difference in signal intensity between the sample 1 and the sample 3 was approximately 25000. However, it was confirmed that the amounts of TSH present in the three samples were the same when comparing the ratios obtained by dividing the signal intensity of the test zone by the signal intensity of the reference zone. That is, there was a difference in viscosity of blood even in the samples having the same TSH concentration according to the patients, and thus the signals in the test zone was able to be different to any great extent. According to the device for the immunological measurement of the present invention, however, the T/R ratio may also be made constant by reflecting changed signals in the test zone into the signal intensity in the reference zone and changing the signals in the test zone at a similar ratio, thereby enabling exact quantitative analysis.

Experimental Example 2

Verification for Reflection of Experimental Environment by Repeated Measurement of Same Sample To determine analysis reproducibility, the signal intensities in the test zone and the reference zone, and coefficients of variation (CV: %) appearing in the T/R ratio were calculated. The coefficient of variation was calculated by the expression: standard deviation/average×100, and the average and the standard deviation were calculated from the results obtained through 5 repeated experiments.

Specifically, from the results in which the amount of TSH present in the sera from the patients was measured using a large-scaled automated immunoassay system (Access 2 analyzer, Beckman Coulter), the samples in which TSH was measured to be at a concentration of 0.00 uIU/mL were selected, and TSH was directly added to concentrations of 5 uIU/mL and 100 uIU/mL (Spiking) to prepare samples A and B, which were then used for experiments. Each of the samples having two different concentrations was injected into five microchips, and analyzed.

30 μL of a test serum sample was dropped through a sample injection port of the microchip, and the microchip was inserted into the device for the immunological measurement according to one exemplary embodiment of the present invention after the lapse of 5 minutes. After approximately 40 seconds, the (quantitative) amount of TSH in the sample and the signal intensity values in the test zone and the reference zone were displayed on a display screen of the measurement device. Also, the coefficients of variation measured using the parameters are listed the following Table 6.

As listed in Table 6, it was revealed that there was a difference in signals in the test zone or the reference zone, and the CV values were greater than 10%, but the CV values reduced to less than 10% when calculating the T/R ratios. That is, it was revealed that the device for the immunological measurement according to one exemplary embodiment of the present invention was able to repeatedly measure the same samples having different concentrations, and thus always show the same results since handling errors by experimenters, a fine difference in amount of an injected sample, and variations of the devices were reflected per se.

Experimental Example 3

Comparison of Data on Samples According to Concentration

The result values of the signal intensities in the thirteen TSH serum samples present within a detection zone, in which the concentration of TSH in a serum measured in Experimental Example 1 by the method for the immunological measurement using the atrazine reference antibody according to one exemplary embodiment of the present invention and the conventional anti-rabbit reference antibody was already known, were analyzed.

30 μL of a TSH serum sample was dropped at a dose of 30 μL through a sample injection port of a microchip, and the microchip was inserted into the measurement device according to one exemplary embodiment of the present invention after the lapse of 5 minutes. After approximately 40 seconds, the (quantitative) amount of TSH in the sample and the signal intensity values in the test zone and the reference zone were displayed on a display screen of the measurement device.

Meanwhile, the measurement method using the conventional anti-rabbit reference antibody was performed in the same manner as described above, except that a microchip manufactured so that an anti-rabbit antibody was fixed in the reference zone, and a probe specifically binding to TSH and a probe specifically binding to the anti-rabbit antibody (an anti-rabbit goat antibody) were fixed in the conjugate zone was used herein (see International Publication No. WO 2013/125855). The results are listed in the following Table 7.

TABLE 7

| TSH concentration | Measurement using atrazine antibody | | | Measurement using conventional anti-rabbit reference antibody | | |
| --- | --- | --- | --- | --- | --- | --- |
| | Test zone | Reference zone | T/R | Test zone | Reference zone | T/R |
| 0 | 3025 | 66201 | 0.046 | 103 | 63356 | 0.002 |
| 0.32 | 4403 | 61931 | 0.071 | 2414 | 71066 | 0.034 |

TABLE 6

| | Sample A | | | Sample B | | |
| --- | --- | --- | --- | --- | --- | --- |
| | Test zone | Reference zone | Ratio (T/R) | Test zone | Reference zone | Ratio (T/R) |
| Cartridge 1 | 15600 | 45870 | 0.340 | 211202 | 66017 | 3.199 |
| Cartridge 2 | 15637 | 48629 | 0.322 | 183114 | 60548 | 3.024 |
| Cartridge 3 | 19661 | 51810 | 0.379 | 148279 | 55952 | 2.650 |
| Cartridge 4 | 17018 | 47024 | 0.362 | 188573 | 60039 | 3.141 |
| Cartridge 5 | 21054 | 68214 | 0.309 | 144859 | 51085 | 2.836 |
| CV (%) | 13.82 | 17.53 | 8.43 | 16.10 | 9.49 | 7.62 |

TABLE 7-continued

| TSH | Measurement using atrazine antibody | | | Measurement using conventional anti-rabbit reference antibody | | |
|---|---|---|---|---|---|---|
| con-centration | Test zone | Reference zone | T/R | Test zone | Reference zone | T/R |
| 1 | 15121 | 65789 | 0.230 | 4474 | 51907 | 0.086 |
| 1.5 | 26448 | 82746 | 0.320 | 5170 | 45527 | 0.114 |
| 2 | 29793 | 76689 | 0.388 | 10007 | 63647 | 0.157 |
| 3 | 56779 | 89275 | 0.636 | 12454 | 60564 | 0.206 |
| 3.38 | 31930 | 66310 | 0.482 | 10466 | 52429 | 0.200 |
| 5.37 | 53908 | 60230 | 0.895 | 21380 | 57541 | 0.372 |
| 6.68 | 53206 | 60901 | 0.874 | 21399 | 46373 | 0.461 |
| 10.16 | 65724 | 56800 | 1.157 | 42264 | 63195 | 0.669 |
| 13.25 | 113709 | 63342 | 1.795 | 56566 | 56710 | 0.997 |
| 16.31 | 126499 | 71101 | 1.779 | 57326 | 50438 | 1.137 |
| 24.52 | 155941 | 62522 | 2.494 | 95615 | 57430 | 1.665 |

As listed in Table 7, it was revealed that, when the samples were measured using the atrazine reference antibody according to one exemplary embodiment of the present invention, the intensities of the signals in each zone and the T/R ratios increased in proportion to the increasing concentration of TSH in the samples.

Therefore, the standard curve was previously plotted for a standard substance, which specifically reacted only in the test zone, according to each concentration, the corresponding T/R ratios were applied to the functions corresponding to the curve to convert the concentration of TSH, thereby to represent the concentration of TSH in the sample obtained from the T/R ratios as a representation value. A graph is plotted for the correlation with the large-scaled automated immunoassay system, and shown in FIG. 5.

As one of tools for analyzing the relationship between parameters, regression analysis undergone the following steps: setting a regression model, estimating a coefficient of the regression model for an actually observed sample, and deducing a linear regression equation exhibiting the relationship between the parameters.

A coefficient of determination was represented by a coefficient indicating to which extent a regression line estimated from such sample observation explains the actually observed sample, for example, determining to which extent the regression line represents an actually observed value to exhibit goodness of fit. In this case, the coefficient of determination represents a value between 0 and 1. Such a coefficient of determination is identical to the product of a correlation coefficient (generally referred to as "r") indicating a degree of correlation between two parameters, and thus is represented by $R^2$ (R-Squared). When it is assumed that $R^2=1$, this means that all the observed values for the samples are present on an estimated regression line, thereby indicating that the estimated regression line fully explains the relationship between the parameters. On the other hand, when it is assumed that $R^2=0$, this means that the estimated regression line does not explain the relationship between the parameters at all.

Figure 5:
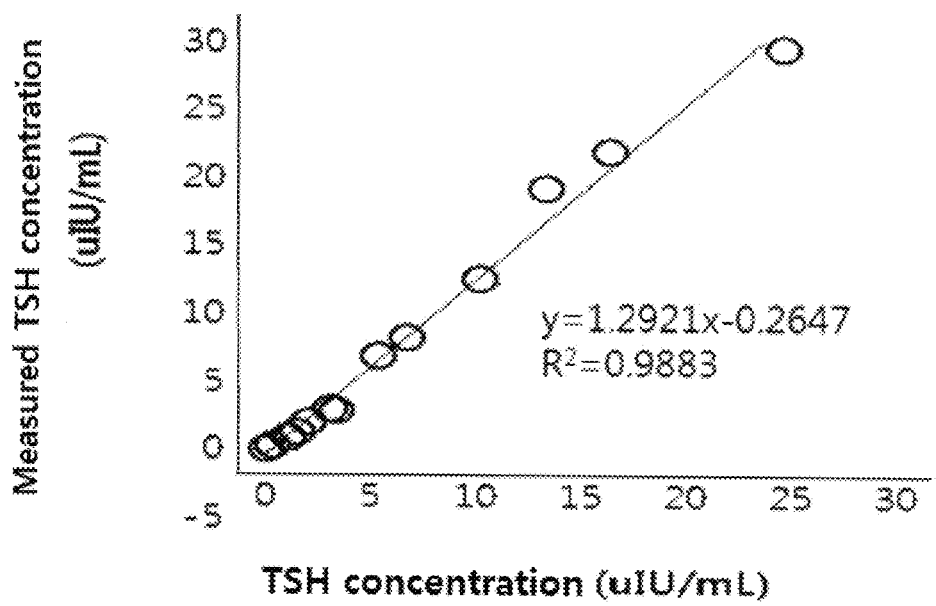
FIG. 5 is a graph plotted for representation values into which TSH concentrations in a sample measured using an atrazine antibody according to one exemplary embodiment of the present invention and a conventional control antibody are converted, respectively.
Figure 5:
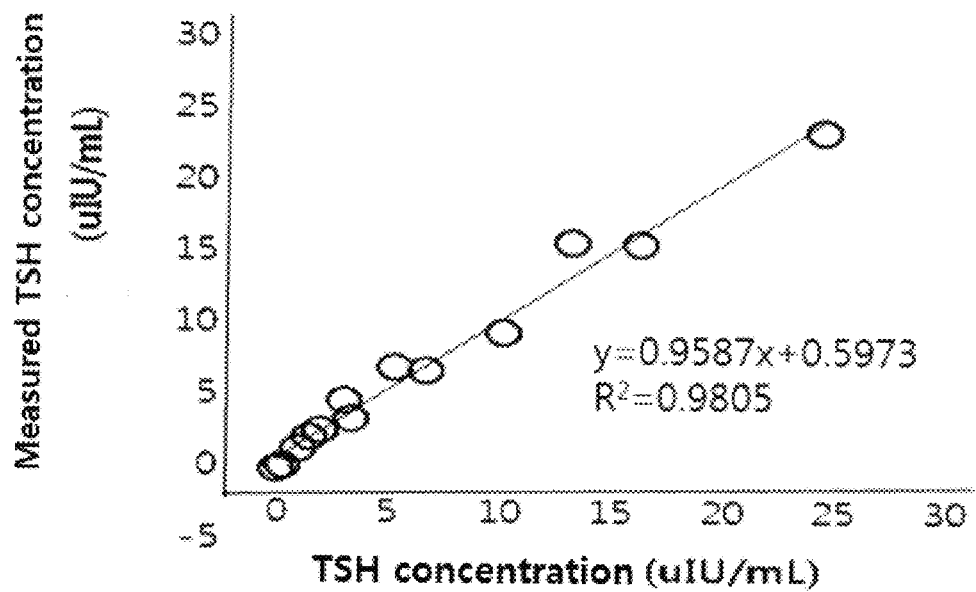

As shown in FIG. 5, it was confirmed that, when the reference antibody according to one exemplary embodiment of the present invention was used, the $R^2$ value was 0.9883, which was greater than an equivalent level, compared to the fact that the $R^2$ value was 0.9805 when the conventional reference antibody including rabbit IgG and anti-rabbit antibody was used.

Experimental Example 4

Comparison Data on Samples According to Measured Temperature

Detection tests were performed on the test serum samples present in the detection zone at one fixed concentration of 5 µIU/mL and an increasing temperatures of 4° C., 15° C., 25° C., 30° C. and 37° C. by a measurement method using the atrazine reference antibody according to one exemplary embodiment of the present invention and the conventional anti-rabbit reference antibody. The measurements were performed using five cartridges per one temperature condition, and an average of the five detection results obtained above was calculated.

Specifically, cartridges and samples were kept at 4° C., 15° C., 25° C., 30° C. and 37° C. for an hour so that the temperatures were set to be identical to the corresponding temperatures. Thereafter, 30 µL of the samples were dropped through sample injection ports of the cartridges, and spread under the corresponding temperature conditions. After the lapse of 5 minutes, a microchip was inserted into a device for the immunological measurement (installed at room temperature). After approximately 40 seconds, the (quantitative) amount of TSH in the sample and the signal intensity values in the test zone and the reference zone were displayed on a display screen of the measurement device. The results are listed in the following Table 8.

TABLE 8

| Number of T/R measurements | T/R signal ratio | | | | |
|---|---|---|---|---|---|
| | 37° C. | 30° C. | 25° C. | 15° C. | 4° C. |
| 1 | 0.328 | 0.389 | 0.327 | 0.279 | 0.269 |
| 2 | 0.363 | 0.285 | 0.306 | 0.275 | 0.308 |
| 3 | 0.334 | 0.304 | 0.398 | 0.254 | 0.261 |
| 4 | 0.367 | 0.295 | 0.305 | 0.326 | 0.248 |
| 5 | 0.321 | 0.284 | 0.358 | 0.252 | 0.295 |
| AVE (average) | 0.34 | 0.31 | 0.34 | 0.28 | 0.28 |
| SD (standard deviation) | 0.021 | 0.044 | 0.040 | 0.030 | 0.025 |
| CV (%) | 6.23 | 14.19 | 11.67 | 10.68 | 8.95 |

As shown in Table 8, it was revealed that, when the atrazine reference antibody according to one exemplary embodiment of the present invention was used, the average values of the T/R ratios were constant with 0.28, 0.28, 0.34, 0.31 and 0.34 as the measured temperatures increased to 4° C., 15° C., 25° C., 30° C. and 37° C., respectively, indicating that the T/R ratios were hardly affected by a change in temperature.

Figure 6:
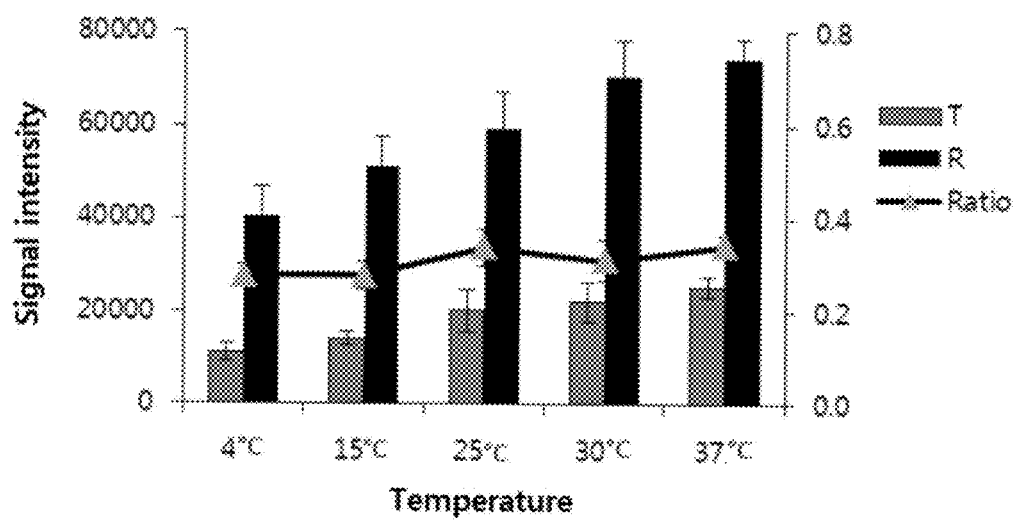
FIG. 6 is a graph plotted for signal intensity values and T/R ratios according to the measured temperature using the anti-atrazine antibody according to one exemplary embodiment of the present invention.

Also, the results from the graph plotted for the signal intensity values in each zone, and the T/R ratios are shown in FIG. 6. The left axis in FIG. 6 represents an intensity of a signal, and the right axis represents a T/R ratio. As shown in FIG. 6, it could be seen that the intensities of the signals increased as the measured temperature increased. This was judged to be due from the fact an antigen/antibody reaction increased according to the temperature.

On the other hand, a microchip for detecting a prostate-specific antigen (PSA) was used to test for the use of the conventional anti-rabbit reference antibody. Test serum samples from patients applied to the outpatient examination room at the Department of Laboratory Medicine of Seoul National University Bundang hospital were used as the blood samples used in this experiment, and a group of patients were selected in a random manner. The group of patients included prostate cancer patients, and the amount of a tumor marker, PSA, in the sera from the patients was measured.

A microchip was manufactured so that a PSA capture antibody was fixed in the test zone, an anti-rabbit antibody was fixed in the reference zone, and a probe specifically binding to PSA, and a probe (i.e., a goat-anti-rabbit antibody) specifically binding to the anti-rabbit antibody were fixed in the conjugate zone, and PSA was detected in the same manner as described in Experimental Example 3 using the microchip manufactured above. The results are shown in FIG. 7.

Figure 7:
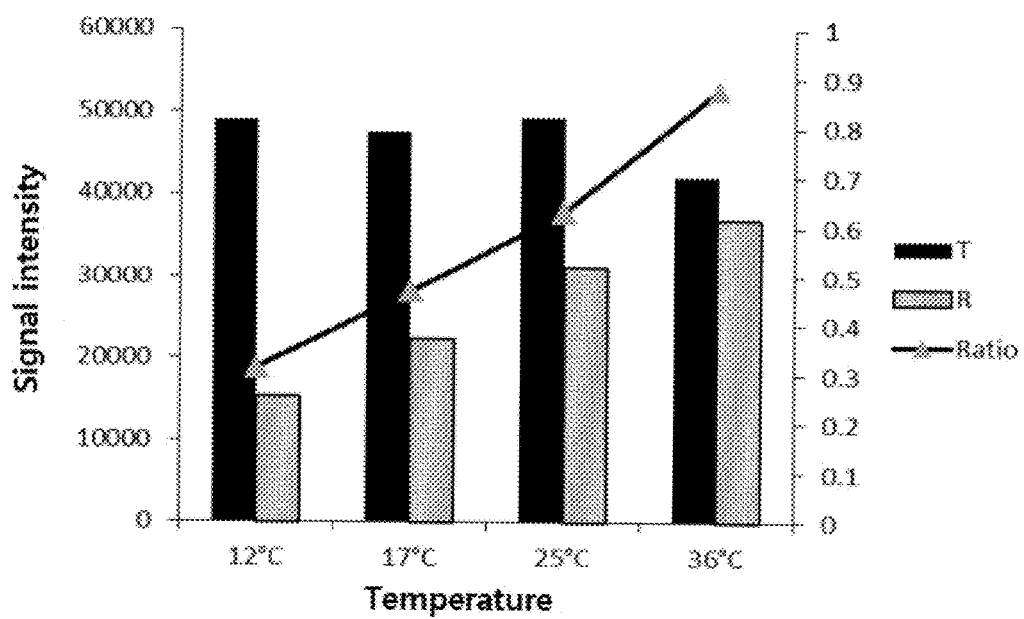
FIG. 7 is a graph plotted for signal intensity values and T/R ratios according to the measured temperature using the conventional anti-rabbit antibody.

As shown in FIG. 7, it could be seen that the signal intensities in the test zone (T) increased according to a change in temperature when the conventional anti-rabbit reference antibody was used, but that the T/R ratios increased since there was hardly a change in the signal intensities in the reference zone (R), resulting in a change in amount of detected PSA according to a change in temperature.

Experimental Example 5

Comparison of Differences in Levels of Reaction of Reference Antibodies According to Measured Temperature Detection tests were performed on the test serum samples present in the detection zone at one fixed concentration of 5 µIU/mL and an increasing temperature of 4° C., 15° C., 25° C., 30° C. and 37° C. by a method of measuring TSH using the atrazine reference antibody according to one exemplary embodiment of the present invention. The measurements were performed under the other condition in the same manner as described in Experimental Example 4.

An average value of the results obtained when repeatedly performed five times at the respective temperatures was measured, and a graph was plotted using the left axis as a signal value in the reference zone. The results are shown in FIG. 8.

Figure 8:
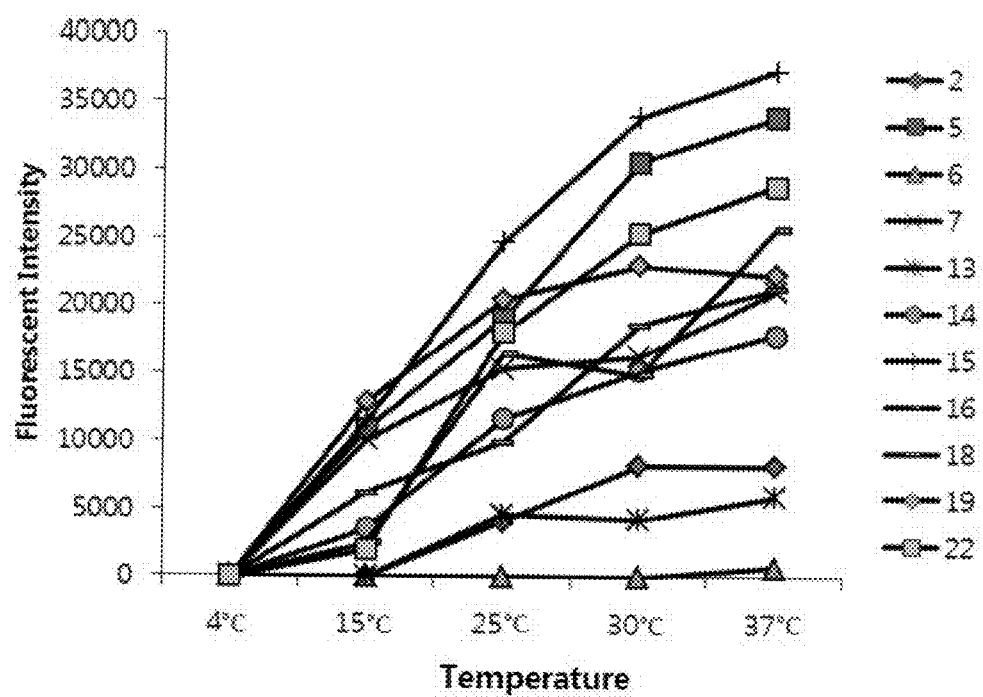
FIG. 8 is a graph plotted for reactivities of the anti-atrazine antibodies according to one exemplary embodiment of the present invention according to the measured temperature.

As shown in FIG. 8, it could be seen that the changes in antigen-antibody binding reactivities of the antibodies according to an increase in temperature were different. For example, the #6 antibody (clone 6) was hardly reactive to a change in temperature, but the #15 antibody (clone 15) was most sensitively reactive to the change in temperature, and the #18 antibody (clone 18) was reactive to the change in temperature at an intermediate level.

As described above, the method or device for the immunological measurement using a hapten and an antibody (reference antibody) biding to the hapten according to one exemplary embodiment of the present invention can be useful in constructing a library of antibodies including antibodies having different reactivities at various temperatures, and selecting and employing reference antibodies having properties similar to reactivity characteristics according to the temperature of the test zone.

The invention claimed is:

1. A method for the immunological measurement of a test substance in a sample using a hapten and a hapten antibody binding to the hapten, comprising the steps of allowing the test substance in the sample to bind to a test probe specific to the test substance to form a complex of the test substance and the test probe in a conjugate zone, and allowing the hapten or the hapten antibody to bind to a reference probe specific to the hapten or the hapten antibody to form a complex of the hapten and the reference probe or a complex of the hapten antibody and the reference probe in the conjugate zone;

spreading the complex of the test substance and the test probe to a test zone, and allowing the complex of the test substance and the test probe to bind to a capture antibody against the test substance;

spreading the complex of the hapten and the reference probe or the complex of the hapten antibody and the reference probe to the reference zone, and allowing the complex of the hapten and the reference probe or the complex of the hapten antibody and the reference probe to bind to the hapten antibody or the hapten;

measuring a detectable signal emitted by the test probe in the test zone through binding with the capture antibody and the reference probe in the reference zone through binding with the hapten or the hapten antibody; and analyzing the signal to measure the test substance in the sample, wherein the hapten antibody comprises i) a heavy-chain variable region CDR1 having an amino acid sequence set forth in SEQ ID NO: 3, ii) a heavy-chain variable region CDR2 having an amino acid sequence set forth in SEQ ID NO: 4, iii) a heavy-chain variable region CDR3 having an amino acid sequence set forth in SEQ ID NO: 5, iv) a light-chain variable region CDR1 having an amino acid sequence set forth in SEQ ID NO: 6, v) a light-chain variable region CDR2 having an amino acid sequence set forth in SEQ ID NO: 7, and vi) a light-chain variable region CDR3 having an amino acid sequence set forth in SEQ ID NO: 8.

2. The method of claim 1, wherein the method is a quantitative analysis of the test substance in the sample.

3. The method of claim 1, wherein the hapten is atrazine, propazine, prometryn, prometon, simazine, simetryn, ipazine, trietazine, or cyanazine.

4. The method of claim 1, wherein the hapten antibody comprises a heavy-chain variable region having an amino acid sequence set forth in SEQ ID NO: 1; and a light-chain variable region having an amino acid sequence set forth in SEQ ID NO: 2.

5. The method of claim 1, wherein the test probe and the reference probe emit the detectable signal.

6. The method of claim 1, wherein the detectable signal of the test probe and the reference probe is a spectrophotometric signal, a visible signal, an electrochemical signal, or an electrically detectable signal.

7. The method of claim 1, wherein the analyzing the signal is carried out by obtaining a ratio of a signal intensity value in the test zone/a signal intensity value in the reference zone.

8. The method of claim 7, wherein the analyzing the signal is carried out by calculating a ratio of a signal intensity value in the test zone/a signal intensity value in the reference zone (T/R ratio) and applying the calculated T/R ratio to the standard curve of T/R ratio and the concentration of the test substance to obtain the concentration of the test substance.

9. The method of claim 1, wherein the method is performed by a device comprising
(1) the conjugate zone in which the test probe specifically binding to the test substance in the sample, and the reference probe specifically binding to the hapten antibody are impregnated together;
(2) the test zone in which the capture antibody specifically binding to the test substance is impregnated; and
(3) the reference zone in which the hapten antibody is impregnated.

10. The method of claim 9, wherein the device utilizes a capillary force, a micro-channel, chromatography, or a nitrocellulose membrane.

11. A device for the immunological measurement of a test substance in a sample using a hapten and a hapten antibody binding to the hapten, wherein the device comprises:
(1) a conjugate zone in which a test probe specifically binding to the test substance in the sample, and a reference probe specifically binding to the hapten are impregnated together;
(2) a test zone in which a capture antibody specifically binding to the test substance is impregnated; and
(3) a reference zone in which the hapten antibody is impregnated,
wherein the test substance, and the hapten each form a complex with the test probe or the reference probe impregnated in the conjugate zone, and spread to the test zone or the reference zone, and
wherein the hapten antibody comprises i) a heavy-chain variable region CDR1 having an amino acid sequence set forth in SEQ ID NO: 3, ii) a heavy-chain variable region CDR2 having an amino acid sequence set forth in SEQ ID NO: 4, iii) a heavy-chain variable region CDR3 having an amino acid sequence set forth in SEQ ID NO: 5; iv) a light-chain variable region CDR1 having an amino acid sequence set forth in SEQ ID NO: 6, v) a light-chain variable region CDR2 having an amino acid sequence set forth in SEQ ID NO: 7, and vi) a light-chain variable region CDR3 having an amino acid sequence set forth in SEQ ID NO: 8.

12. The device of claim 11, wherein the hapten is atrazine, propazine, prometryn, prometon, simazine, simetryn, ipazine, trietazine, or cyanazine.

13. The device of claim 11, wherein the device uses a capillary force, a micro-channel, chromatography, or a nitrocellulose membrane.

14. The device of claim 11, wherein the hapten antibody comprises a heavy-chain variable region having an amino acid sequence set forth in SEQ ID NO: 1; and a light-chain variable region having an amino acid sequence set forth in SEQ ID NO: 2.

15. The device of claim 11, wherein the test probe and the reference probe emit a detectable signal.

16. The device of claim 15, wherein the detectable signal of the test probe and the reference probe is a spectrophotometric signal, a visible signal, an electrochemical signal, or an electrically detectable signal.

* * * * *